United States Patent
Jakus et al.

(10) Patent No.: US 11,904,071 B2
(45) Date of Patent: Feb. 20, 2024

(54) SURGICALLY-FRIENDLY TISSUE PAPERS FROM ORGAN-SPECIFIC DECELLULARIZED EXTRACELLULAR MATRICES

(71) Applicant: Northwestern University, Evanston, IL (US)

(72) Inventors: Adam E. Jakus, Chicago, IL (US); Ramille N Shah, Hinsdale, IL (US)

(73) Assignee: NORTHWESTERN UNIVERSITY, Evantson, IL (US)

( * ) Notice: Subject to any disclaimer, the term of this patent is extended or adjusted under 35 U.S.C. 154(b) by 451 days.

(21) Appl. No.: 17/330,762

(22) Filed: May 26, 2021

(65) Prior Publication Data

US 2021/0275724 A1    Sep. 9, 2021

Related U.S. Application Data

(62) Division of application No. 16/461,461, filed as application No. PCT/US2017/062218 on Nov. 17, 2017, now Pat. No. 11,045,581.

(Continued)

(51) Int. Cl.
*A61L 27/36* (2006.01)
*A61L 27/24* (2006.01)
(Continued)

(52) U.S. Cl.
CPC ........... *A61L 27/3633* (2013.01); *A61L 27/24* (2013.01); *A61L 27/3804* (2013.01); *A61L 27/3826* (2013.01); *A61L 27/3834* (2013.01); *A61L 27/3873* (2013.01); *A61L 27/3882* (2013.01); *A61L 27/3895* (2013.01);
(Continued)

(58) Field of Classification Search
None
See application file for complete search history.

(56) References Cited

U.S. PATENT DOCUMENTS

| 8,535,719 | B2 | 9/2013 | Badylak et al. |
| 8,691,276 | B2 | 4/2014 | Badylak et al. |

(Continued)

FOREIGN PATENT DOCUMENTS

| WO | 2015175880 A1 | 11/2015 |
| WO | 2016123362 A1 | 8/2016 |

OTHER PUBLICATIONS

Badylak et al., "Extracellular matrix as a biological scaffold material: Structure and function," Acta Biomaterialia, vol. 5, 2009, pp. 1-13.

(Continued)

*Primary Examiner* — Javier G Blanco
(74) *Attorney, Agent, or Firm* — Hahn Loeser & Parks LLP

(57) ABSTRACT

Provided herein are inks including decellularized extracellular matrix (dECM) particles and scaffolds made from the inks. Also provided are methods of making the scaffolds and applications for the scaffolds. In an embodiment, a porous scaffold comprises dECM particles and an elastomer, wherein the scaffold is planar having a thickness of about 100 μm or greater, the scaffold comprises irregularly shaped pores having a random orientation and distribution throughout the scaffold, and the scaffold is free of crosslinking between the molecular components of the scaffold.

22 Claims, 13 Drawing Sheets

Related U.S. Application Data

(60) Provisional application No. 62/424,263, filed on Nov. 18, 2016.

(51) Int. Cl.
    *B33Y 10/00*     (2015.01)
    *B33Y 80/00*     (2015.01)
    *A61L 27/38*     (2006.01)
    *A61L 27/48*     (2006.01)
    *A61L 27/56*     (2006.01)
    *B33Y 70/00*     (2020.01)

(52) U.S. Cl.
CPC ............... *A61L 27/48* (2013.01); *A61L 27/56* (2013.01); *B33Y 10/00* (2014.12); *B33Y 80/00* (2014.12); *A61L 2430/22* (2013.01); *A61L 2430/30* (2013.01); *A61L 2430/40* (2013.01); *B33Y 70/00* (2014.12); *C12N 2533/90* (2013.01)

(56) References Cited

U.S. PATENT DOCUMENTS

| | | | | |
|---|---|---|---|---|
| 8,835,174 | B2 * | 9/2014 | Fette | A61B 17/08 435/395 |
| 9,327,448 | B2 | 5/2016 | Shah et al. | |
| 2005/0129730 | A1 * | 6/2005 | Pang | A61L 27/56 424/423 |
| 2005/0222661 | A1 | 10/2005 | Case et al. | |
| 2008/0268019 | A1 | 10/2008 | Badylak et al. | |
| 2010/0222882 | A1 | 9/2010 | Badylak et al. | |
| 2010/0267143 | A1 | 10/2010 | Park et al. | |
| 2014/0023723 | A1 | 1/2014 | Leach et al. | |
| 2014/0335144 | A1 | 11/2014 | Ward et al. | |
| 2015/0037385 | A1 | 2/2015 | Shah et al. | |
| 2015/0231302 | A1 | 8/2015 | Duvall et al. | |
| 2017/0360992 | A1 | 12/2017 | Ameer et al. | |

OTHER PUBLICATIONS

Laronda, Monica M., et al., "Alginate encapsulation supports the growth and differentiation of human primordial follicles within ovarian cortical tissue." Journal of assisted reproduction and genetics 31.8 (2014): 1013-1028.

Jakus, Adam E., et al., "Three-dimensional printing of high-content graphene scaffolds for electronic and biomedical applications." ACS nano 9.4 (2015): 4636-4648.

Laronda et al., "Initiation of puberty in mice following decellularized ovary transplant," Biomaterials, May 2015; vol. 50, pp. 20-29.

Jakus et al., "Surgically-Friendly Tissue Papers Derived from Tissue- and Organ-Specific Decellularized Extracellular Matrices," World Biomaterials Congress: Montreal, Canada Northwestern University Postdoctoral Forum, May 18, 2016, p. 1.

Jakus, Adam E., et al., "Hyperelastic bone: A highly versatile, growth factor free, osteoregenerative, scalable, and surgically friendly biomaterial." Science translation medicine 8.358 (2016): 358ra127-358ra127. (downloaded from http://stm.sciencemag.org/ on Sep. 28, 2016), 41 pgs.

The International Search Report and Written Opinion issued in International patent application No. PCT/US2017/062218 dated Feb. 9, 2018, pp. 1-8.

\* cited by examiner

SURGICALLY-FRIENDLY TISSUE PAPERS FROM ORGAN-SPECIFIC DECELLULARIZED EXTRACELLULAR MATRICES

CROSS-REFERENCE TO RELATED APPLICATIONS

The present application is a divisional patent application of U.S. patent application Ser. No. 16/461,461, filed May 16, 2019, which is a National Stage application of International Application No. PCT/US2017/062218, filed Nov. 17, 2017, which claims priority to and the benefit of U.S. Provisional Patent Application No. 62/424,263, filed Nov. 18, 2016, all of which are incorporated herein by reference.

BACKGROUND

Decellularized Extracellular Matrices (dECMs) have emerged as an extremely promising class of tissue/organ-specific biomaterials with potential applications in whole organ replacement and tissue/organ engineering and regeneration. There have been two major approaches for utilizing dECM. The first involves the decellularization of whole organs followed by recellularization and use. The second involves the decellularization of tissue and organ sections and utilizing the resulting dECM as a raw material for making biomaterials such as injectable and rigid gels and coatings for synthetic polymers.

SUMMARY

Provided herein are inks including decellularized extracellular matrix (dECM) particles and scaffolds made from the inks. Also provided are methods of making the scaffolds and applications for the scaffolds.

In one aspect, a scaffold is provided. In an embodiment, a porous scaffold is provided which comprises dECM particles and an elastomer, wherein the scaffold is planar having a thickness of about 100 µm or greater, the scaffold comprises irregularly shaped pores having a random orientation and distribution throughout the scaffold, and the scaffold is free of crosslinking between the molecular components of the scaffold.

In another aspect, a method of forming a scaffold is provided. In an embodiment, a method comprises depositing an ink onto the surface of a substrate by pouring or flowing the ink while applying no force to the ink other than gravity, the ink comprising an elastomer; an organic solvent system comprising an evaporant, a surfactant, and a plasticizer; and dECM particles; and removing the organic solvent system from the ink to form the scaffold.

In another aspect, a method of using a scaffold is provided. In an embodiment, a method comprises implanting a scaffold in vivo into a mammalian patient or grafting the scaffold in vivo onto a tissue or an organ of the mammalian patient.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings.

DETAILED DESCRIPTION

Figure 1:
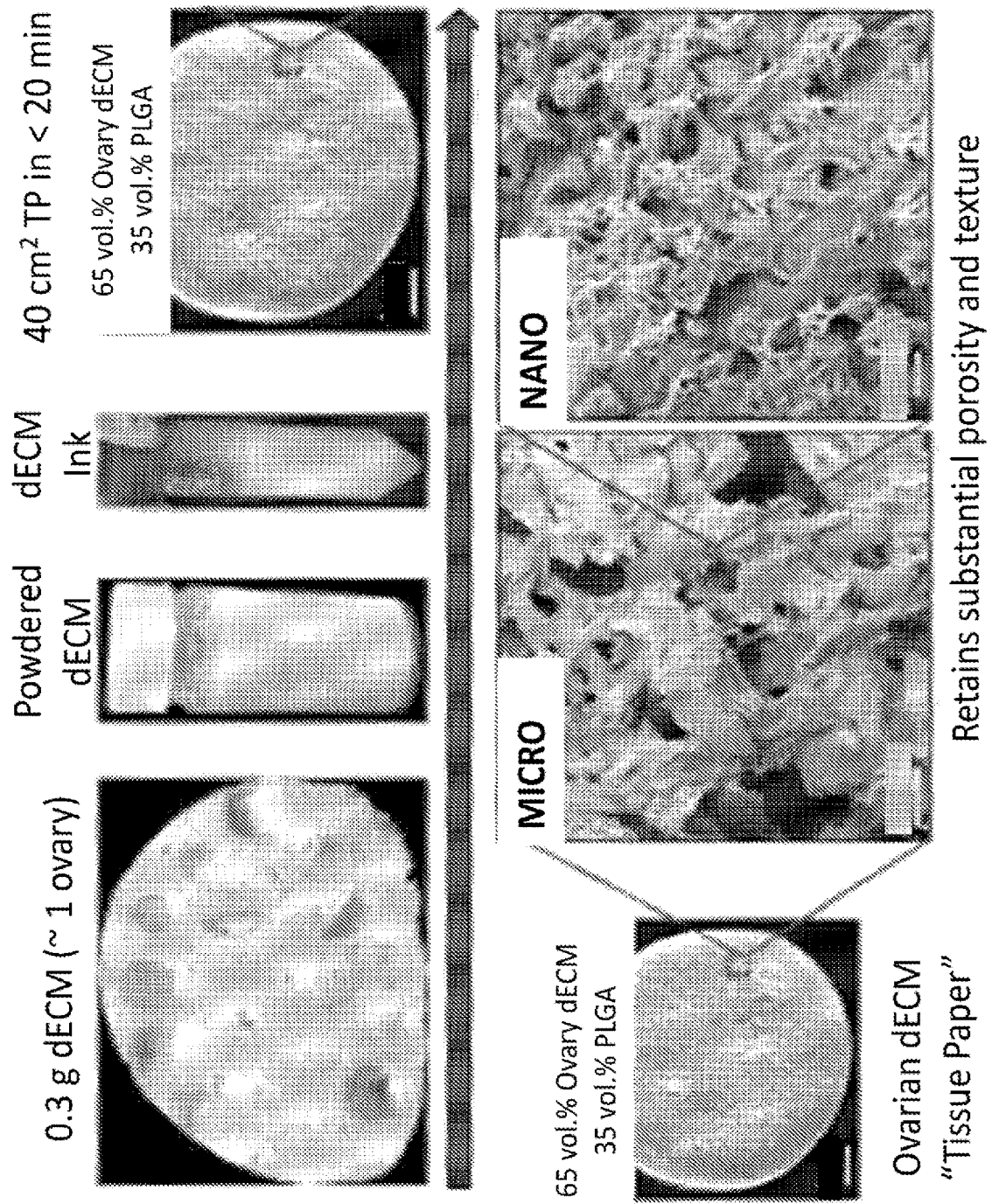
FIG. 1 illustrates the formation of ovary decellularized extracellular matrix (dECM) tissue paper (TP) (top). Also included are images showing the microstructure and the nanostructure of the TP (bottom).

Provided herein are inks including decellularized extracellular matrix (dECM) particles and scaffolds made from the inks. Also provided are methods of making the scaffolds and applications for the scaffolds.

The inks represent a new approach for utilizing dECMs to provide biomedical materials, the scaffolds. At least some embodiments of the scaffolds exhibit one or more of the following advantages: result from a universal, simple, inexpensive, scalable fabrication process applicable to a broad range of tissues and organs; extended shelf life; tissue specific bioactivity; mechanical robustness and compatibility with surgical techniques such as rolling, cutting, suturing, folding; high absorbency; readily integrated without being encapsulated; and customizable platform for delivering a variety of additives (e.g., drugs). These and other advantages are further described below.

In some instances in the present disclosure, the scaffolds may be referred to as "tissue paper."

The inks for forming the scaffolds include an elastomer, an organic solvent system and dECM particles. The elastomer may be a biocompatible compound, i.e., one suitable for biological applications. The elastomer functions to hold the dECM particles together in the scaffold. Various elastomers may be used depending upon the desired application and/or the desired mechanical properties for the scaffold (e.g., elasticity). Illustrative elastomers include polyesters, poly (meth)acrylates, polyethylene glycols, or combinations thereof. Illustrative polyesters include polylactic acid (PLA), glycolic acid, copolymers of PLA and glycolic acid (i.e., polylactic-co-glycolic acid (PLGA)), and polycaprolactone (PCL). The ink may include various amounts of elastomer, based on the total solids content of the inks. The amount may be selected depending upon the desired application and/or the desired mechanical properties. In embodiments, the amount is in the range of from about 5 vol % to about 95 vol %, based on the total solids content. This includes an amount in the range of from IS vol % to about 80 vol %, or from 20 vol % to about 70 vol %.

The organic solvent system includes an evaporant, a surfactant, and a plasticizer. By "evaporant" it is meant an organic solvent that has a sufficiently high vapor pressure so as to evaporate rapidly at room temperature (i.e., about 20 to 25° C.) and atmospheric pressure. Illustrative evaporants include dichloromethane, chloroform and combinations thereof. The organic solvent system may include various amounts of the evaporant, based on the total volume of the organic solvent system. In embodiments, the amount is in the range of from about 10 vol % to about 95 vol %, based on the total volume. An illustrative surfactant is dibutylphthalate. An illustrative plasticizer is 2-butoxyethanol. The organic solvent system may include various amounts of the surfactant and the plasticizer. The mass ratio of the surfactant:plasticizer may be in the range of from about 1:20 to about 20:1. The ink may include various amounts of the organic solvent system. The amount may be selected to provide the ink with a desired viscosity for use in the method described below. Illustrative viscosities include those in the range of from about 0.0005 Pa·s to about 100 Pa·s. The organic solvent system may consist essentially of, or consist of, the evaporant(s), the surfactant(s) and the plasticizer(s).

The dECM particles in the ink are obtained by processing decellularized extracellular matrices. A variety of types of decellularized extracellular matrices (and thus, a variety of ty pes of dECM particles) may be used, including those derived from tissues and organs such as liver, kidney, cardiac, skin, muscle, ovary, uterus, bladder, prostate, testicle, cervix, lung, pancreas, bone, peripheral and central nerves, etc. An illustrative process for obtaining dECM particles from native tissues/organs is described in the Example, below. (Also see FIG. 9.) The ink may include various amounts of the dECM particles, based on the total solids content of the ink. The amount may be selected depending upon the desired application and/or the desired mechanical properties. In embodiments, the amount is in the range of from about 5 vol % to about 95 vol %, based on the total solids content. This includes an amount in the range of from about 20 vol % to about 90 vol %, or from about 30 vol % to about 80 vol %.

The size (e.g., 1 nm or less, greater than 5 mm) and shape (e.g., spherical or irregular) of the dECM particles is not particularly limited.

The ink may include other additives in various combinations and amounts, depending upon the desired application. Any of the particles described in International Publication WO 2015/175880, U.S. Pat. No. 9,327,448, and U.S. Pat. Pub. No. 20150037385, each of which is hereby incorporated by reference in its entirety, may be used. Illustrative additives include calcium phosphates (e.g., hydroxyapatite) and conductive materials (e.g., graphene). Other additives include drugs, antibiotics, antimicrobial agents, bioactive factors, etc.

The ink may consist essentially of, or consist of, the elastomer, the organic solvent system, the dECM particles, and optionally, the additives. The ink may be characterized as being free of water, i.e., the ink is a non-aqueous ink. By "free" it is meant substantially free such that the amount of water may not be exactly zero but the amount is so small so as to have no material effect on the ink or a scaffold made from the ink. The ink may be characterized as being free of cross-linking between the molecular components of the ink. By "free" it is meant substantially free analogous to the meaning set forth above. As such, the ink would not be considered a gel or a hydrogel.

It is noted that the disclosed inks may have significantly lower viscosities than would be suitable for 3D-printing applications since at such low viscosities, they cannot be 3D-printed (i.e. cannot be continuously extruded, self-supporting upon extrusion, and rapidly drying).

As noted above, the inks may be used to form a scaffold. A method of forming a scaffold may include depositing any of the disclosed inks onto a substrate and removing the organic solvent system from the ink. Removal of the organic solvent system provides a solid structure. i.e., the scaffold. The deposition may be carried out by simply pouring or flowing the ink onto the substrate. In this type of deposition, no additional forces are applied to the ink during deposition other than gravity. By "no additional forces" it is meant substantially no additional forces analogous to the meaning set forth above. However, the substrate may apply a resistive force on the ink during deposition which may vary depending upon the configuration of a substrate, as further described below. The external morphology (e.g., overall shape, shape of external surfaces) of the scaffold is determined by the substrate upon which the ink is deposited as well as the surface tension of the ink.

The present type of deposition is distinguished from casting techniques such as spin-casting in which additional force is applied to the ink (i.e., centrifugal force) during deposition to form a thin (e.g., 1 pin or less) film. The present type of deposition is also distinguished from extrusion techniques such as three-dimensional (3D) printing in which inks are forced (e.g., by pressure) through small diameter nozzles, e.g., to form high aspect ratio structures. The present type of deposition is further distinguished from dip-coating, where a target substrate is brought into contact with a coating composition and requires dynamic, controlled extraction of the substrate from the printing medium to yield a film. Dip-coating requires that the coating composition dry very quickly, which implies high viscosity/lower solvent content to particle/polymer content.

Various substrates may be used, including those formed from various materials and having various configurations. In embodiments, the substrate is planar. The substrate may have a smooth and flat surface. However, the surface of the substrate may include features such as ridges, projections, edges, recesses, depressions, cavities, etc. Such substrates are useful so as to impart complementary features onto an external surface of the scaffold. In some instances in the present disclosure, the substrate may be referred to as a mold. For example, in embodiments, the substrate may be an object formed using additive manufacturing, e.g., 3D-printing, such as a mold formed from the digital image shown in FIG. 8.

The deposition may be carried out at room temperature and atmospheric pressure. The organic solvent system removal may be carried out at room temperature or an elevated temperature and for a time sufficient to remove all of the organic solvent system. By "all" it is meant substantially all analogous to the meaning set forth above.

Because the organic solvent system is removed from the ink in order to form the scaffold, the composition of the scaffold is determined by the selection and relative amounts of the elastomer, the dECM particles, and optionally, any remaining additives. In embodiments, the scaffold includes from about 5% to about 95% by weight elastomer and from about 5% to about 95% by weight dECM particles, based on the total solids content. The scaffold may consist essentially of, or consist of, the elastomer and the dECM particles. The scaffold may be characterized as being dry, by which it is meant the scaffold is free of liquid, including water. The scaffold may be characterized as being free of cross-linking (physical or chemical cross-linking) between the molecular components of the scaffold. As such, the scaffold would not be considered a gel or a hydrogel or a chemically fixed tissue such as an allograft. In both cases, by "free" it is meant substantially free analogous to the meaning set forth above.

The scaffold may be further distinguished from a gel or hydrogel by its mechanical properties has compared to those of hydrogels or gels. Hydrogels may be defined as having highly viscoelastic mechanical behavior, which means they have a clear liquid to solid mechanical behavior transition as result of mechanical stimuli (this differentiates a gel from solids that happen to be porous and wet. e.g., a sponge). The disclosed scaffolds may be characterized as thin sponges. Even hydrated, the scaffolds may not exhibit any clear viscoelastic solid-liquid or liquid-solid property transition.

Gels are solid-like under ambient conditions (no applied mechanical stress), but will flow and become liquid-like under the influence of a mechanical load. As noted above, hydrated scaffolds may be characterized as wet porous solids (similar to a sponge or clothing when wet) and do not undergo a solid-to-liquid transition upon application of mechanical stress.

Figure 10:
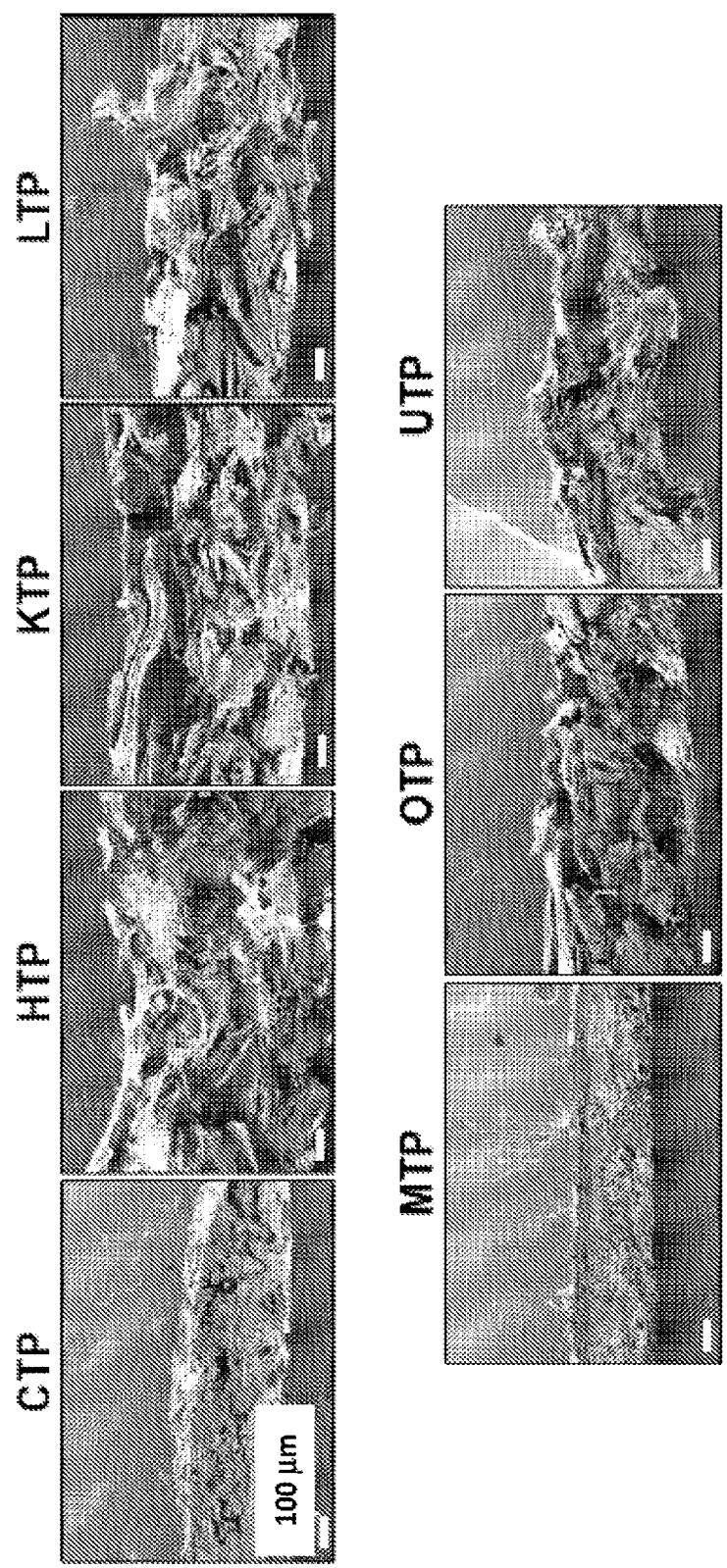
FIG. 10 shows additional representative scanning electron micrographs of dry TP cross-sections (C=collagen; H=heart; K=kidney; L=liver; M=muscle; O=ovary; U=uterus; scale bar is 100 µm).

The scaffold may be characterized by a length (the largest dimension across a surface of the scaffold); a width (the second largest dimension across the surface of the scaffold); and a thickness (the cross-sectional dimension from the top (uppermost) surface of the scaffold to the bottom (lowermost) surface). Depending upon the shape of the scaffold, the width may be a diameter. (See FIG. 2.) Cross-sectional thicknesses of illustrative scaffolds are shown in FIGS. 3 and 10. The length and width are not particularly limited but are generally much greater than the thickness. As such, the scaffold may be characterized as being planar. The terms "paper," "sheet," and "laver" and the like may be used to describe the form of the scaffold. The thickness may be an average thickness value as determined at various locations across the surface of the scaffold. In embodiments the thickness is about 100 μm or greater. This includes embodiments in which the thickness is about 150 μm or greater, about 200 m or greater, or about 250 μm or greater. This includes embodiments in which the thickness is in the range of about 50 μm to about 4 mm, about 100 sim to about 1000 μm, or about 100 μm to about 500 μm. These thicknesses are considerably greater than the thicknesses of spin-cast films (e.g., 1 μm or less) or dip-coated films (e.g., 25 μm or less). As further discussed below, these thickness can be provided in a single deposition step by contrast to methods using multiple deposition steps to build up multiple layers of material.

The scaffold may be characterized by its external morphology. e.g., its overall shape and the shape of its external surfaces (e.g., the top and bottom surfaces). In embodiments, the top and bottom surfaces of the scaffold are flat. This characterization may apply even if the surfaces exhibit some shape/texture (e.g., microstructure or nanostructure) due to their internal morphology as described below. By way of illustration, the scaffold surfaces shown in FIGS. 2, 3 and 10, from scaffolds formed on planar substrates having flat and smooth surfaces, may be considered to be flat even though those surfaces exhibit varying degrees of microstructure/nanostructure as described below. In other words, despite the microstructure/nanostructure, the scaffold surfaces appear flat on the macroscale.

In other embodiments, the top and/or bottom surfaces may include ridges, projections, edges, depressions, recesses, cavities, etc., e.g., formed from complementary features on the substrates as described above. However, these complementary features generally have significantly larger dimensions than the microstructure/nanostructure of a scaffolds surfaces. At the same time, these complementary features generally have significantly smaller dimensions than the overall dimensions of the scaffold. By way of illustration, a scaffold formed from the mold of FIG. 8 will have complementary depressions across its surfaces. This scaffold may still be considered planar even though it includes the depressions as the width/length of the scaffold are much greater than its thickness and since the depressions are smaller than the width/length/thickness of the scaffold.

The scaffold may be characterized by its internal morphology. The internal morphology depends, at least in part, upon the morphology of the extracellular matrices from which the scaffold is derived. For example, the scaffold is generally porous, but the shape, size, orientation and distribution of the pores may vary. (See FIGS. 2, 3 and 10.) The pores of the scaffold may be characterized as being elongated; layered; irregularly shaped; randomly distributed and oriented; and/or interconnected forming tortuous channels throughout the scaffold. The channels may be discontinuous or continuous. By contrast, films formed from spin-casting and dip-coating generally are not porous.

Although the scaffold may be porous, it may be characterized as being a continuous, monolithic structure as distinguished from 3D-printed materials which may be composed of discrete, identifiable structures which have been fused together to form the material. In addition, the random, irregular and tortuous nature of the pores of the scaffolds may further distinguish them from the pores of 3D-printed materials. The continuous, monolithic scaffolds are also distinguished from multilayer constructs formed by repeatedly depositing layers of material (e.g., via spin-casting or dip-coating). In the latter case, the interfaces between adjacent deposited layers will be discernable.

The scaffold may be characterized by its mechanical properties, including its Young's modulus and its ultimate tensile strength. Young's modulus and ultimate tensile strength may be determined as described in the Example, below. These properties may depend upon the particular tissue or organ from which the scaffold was derived. For example, non-structural tissues/organs, such as ovary, kidney, liver, heart and uterus may have Young's modulus/ultimate tensile strength values which are smaller than structural tissues/organs such as muscle and skin. These properties also depend upon whether the scaffold is dry or has been (re)hydrated. In embodiments, the dry scaffold material is characterized by a Young's modulus of from about 500 kPa to about 100 MPa. This is b) contrast to the Young's modulus of soft-tissue organs (about 10 Pa to about 1 MPa) from which the dry scaffold material is derived. In embodiments, the dry scaffold material is characterized by an ultimate tensile strength of from about 1 kPa to about 5 MPa. This is by contrast to the ultimate tensile strength of organs (about 0.01 Pa to 10 kPa) from which the dry scaffold material is derived. Due to their mechanical strength, the scaffolds are sufficiently robust to be subjected to a variety of deformation steps such as twisting, crumpling, cutting, folding, stitching, suturing, etc., without breaking, crumbling, flaking, tearing, etc. At the same time, despite the difference in mechanical properties as compared to the organ/tissue from which the scaffolds are derived, the inventors have found that the scaffolds are surprisingly able to support the attachment, growth, and proliferation of cells. Similarly, despite the difference in mechanical properties, the inventors have found that the scaffolds are able to support tissue that adheres and remains viable (live) over extended periods of time with excellent integration with host tissue/organs.

The scaffold may be characterized by its absorbency. The absorbency may be determined as described in the Example below and may be reported as the ([wet weight−dry weight]/[dry weight])*100. In embodiments, the absorbency is in the range of from about 5% to about 500%. This includes an absorbency in the range of from about 50% to about 500% or from about 100% to about 500%.

Individual planar scaffolds may be stacked or laminated together to form a larger construct. Individual planar scaffolds in the construct may include the same or different types of dECM particles. Individual planar scaffolds may be adhered or fused to one another using an organic solvent such as dichloromethane. Composite structures including a scaffold and another object, e.g., a 3D-printed object, are also provided. The other object may be formed from a variety of materials, including biocompatible materials (e.g., hyperelastic bone) and conductive materials (e.g., graphene).

The scaffolds have a variety of uses. Scaffolds may be used as substrates for the attachment, growth and proliferation of a variety of cells. (See FIG. 7.) Illustrative cells include human mesenchymal stem cells, hematopoetic stem cells, embryonic stem cells, induced pluripotent stem cells, osteoblasts, chondrocytes, fibroblasts, endothelial cells, myocytes, hepatocytes, etc. Cells also include supracellular units, such as follicles or islets. e.g., ovarian follicles or pancreatic islets. Known techniques may be used for seeding and culturing the cells (also see those described in the Example, below). Similarly, scaffolds may be used as substrates to support the attachment, survival, and function of a variety of tissues, e.g., ovarian cortical tissue and muscle tissue. (See FIG. 11.) Scaffolds may be used as substrates for the deposition of other materials, e.g., 3D-printable inks such as those described in International Publication WO2015/175880, U.S. Pat. No. 9,327,448, and U.S. Pat. Pub. No. 20150037385, each of which has been incorporated by reference and in International Publication WO2016123362, which is hereby incorporated by reference in its entirety. The scaffolds may also be used to form composite structures with another object. e.g., a 3D-printed object.

In view of these and other uses, the scaffolds find applications in one or more of the following: tissue and organ specific grafting (patching and repairing damaged/bleeding tissues and organs); treatment of traumatic wounds; local wound care; local flap creation/augmentation; free flap creation/augmentation; fertility preservation (preserve and mature ovarian follicles in vitro); ovarian transplant/ovarian transplant aid/support; tissue and organ specific grafts for tissue replacement (necrotic or missing tissues); plastic surgery and reconstruction; bioactive bandaids, 3D-printing substrates for other biomaterials (i.e. graphene "nerves" onto muscle TP); "grafts" for other biomaterials (i.e. muscle TP on 3D-printed bone materials); In vitro healthy or diseased tissue and organ models; In vivo healthy or diseased tissue and organ models.

EXAMPLE

Example 1

This Example illustrates a new, highly comprehensive approach to tissue- and organ-specific, surgically-friendly, shelf-friendly, scalable biomaterial design and development using decellularized tissues and organs and the resulting extra cellular matrices. A variety of tissue papers (TPs) can be synthesized from polylactic-co-glycolic acid (PLGA) (a biomedical elastomer), a tri-solvent mixture including of a surfactant, plasticizer, and evaporant and decellularized extracellular matrix (dECM) powders. dECM powders are obtained by decellularizing fresh tissues and organs followed by lyophilization and mechanical milling and sieving. Using this process, we demonstrate the fabrication of six tissue specific TPs made from heart (HTP), kidney (KTP), liver (LTP), muscle (MTP), ovary (OTP), and uterus (UTP), in addition to a generic TP created from purified type I collagen (CTP). Tissue paper fabrication is independent of tissue or organ source or type and is performed entirely under ambient conditions. The resulting tissue papers, which are approximately 65 vol. % dECM and 35 vol. % PLGA are mechanically robust in both dry and wet states, highly absorbent, shelf-stable, and promote human mesenchymal stem cell adhesion, proliferation, and differentiation. The TPs can be cut, folded, rolled, sutured, etc.; all manipulations that make them surgically friendly, unlike dECM gels and solutions. Although there is an extensive variety of applications for the TPs depending on the tissue target, we illustrate one such application in detail; human ovarian cortical strip culture. In this case, ovary tissue paper, when used as a culture substrate, promotes the survival and function of human ovarian tissue in vitro. Beyond individual applications for TPs, we also demonstrate that TPs are highly versatile with respect to fabrication, and are also compatible with previously described 3D-printed biomaterials.

Tissue Paper (TP) Fabrication

Tissue Papers (TPs) were synthesized from inks including multiple solvents as well as a biomedical elastomer (such as PLGA) and dECM-containing powder. To obtain dECM powders, fresh porcine (p) heard, liver, kidney, skin and muscle and bovine (b) ovaries and uteri are cut into pieces, decellularized in 0.5% SDS over 2-3 days, washed, lyophilized, and milled. The resulting dECM powders are then used to create the inks, which in this case are cast into planar molds and allowed to dry for several minutes, yielding the Tissue Papers (70 vol. % dECM solids volume, 30 vol. % PLGA). The TPs are washed and sterilized in ethanol and PBS prior to biological use or testing. Collagen Paper derived from purified bovine collagen flakes (Sigma Aldrich) are utilized as a control.

Figure 9:
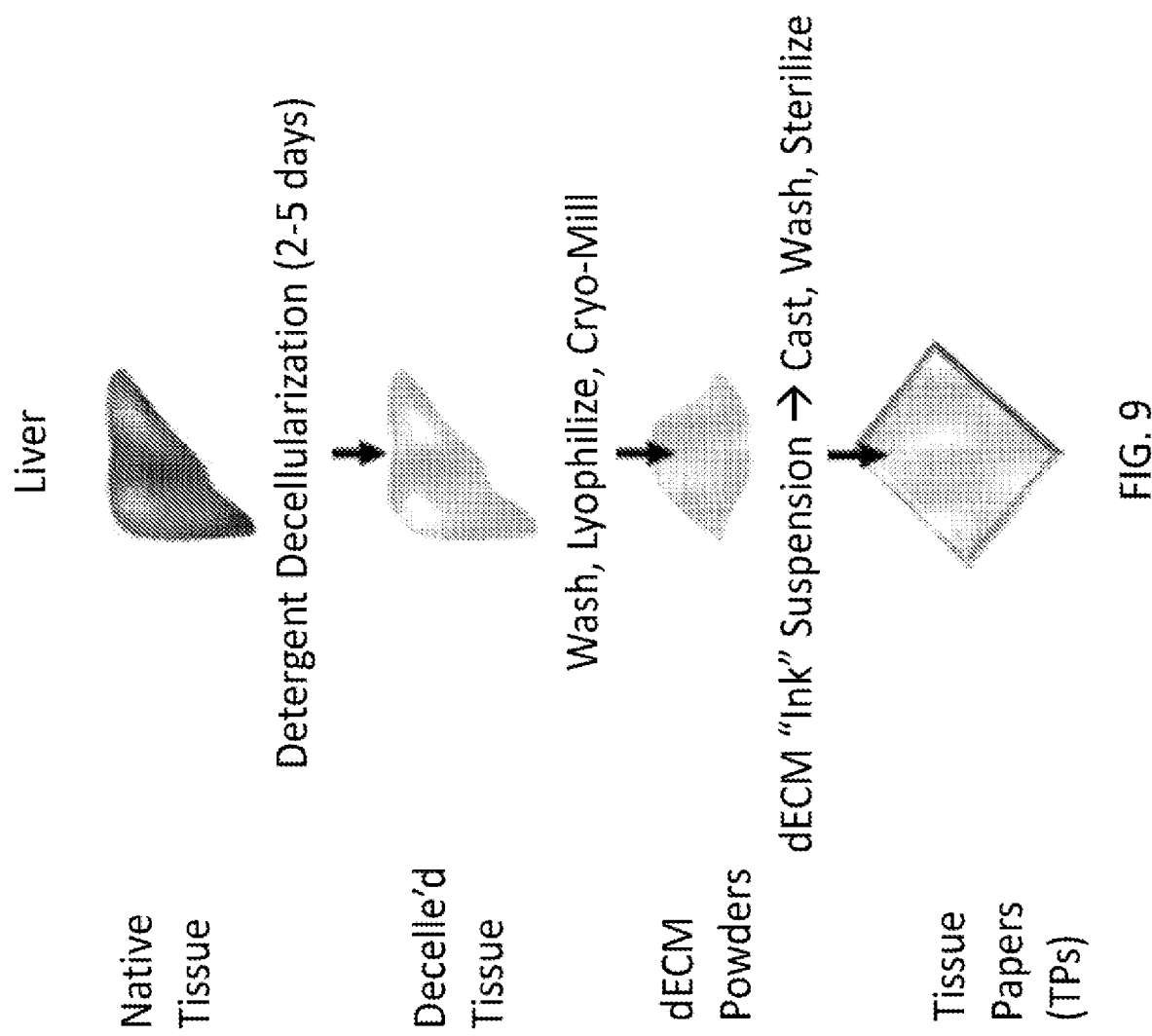
FIG. 9 shows a schematic of the tissue paper fabrication process using liver as an illustrative example (other organs such as heart, kidney, muscle, skin, ovary, uterus may be used).

FIG. 9 shows a schematic of the tissue paper fabrication process using liver as an illustrative example (other organs such as heart, kidney, muscle, skin, ovary, uterus may be used). FIG. 1 shows an example of a decellularized bovine ovary (0.3 g), milled into power, transformed into an ink and cast into an ovary dECM tissue paper (40 cm$^2$ TP including 65 vol. % ovary dECM and 35 vol. % PLGA obtained in less than 20 minutes; scale is 1 cm). As shown in the zoomed in images (MICRO, scale is 200 μm and NANO, scale is 250 nm), the ovary dECM TP retains substantial porosity and texture. About 1 g of dECM can yield approximately 120 cm$^2$ of tissue paper. FIG. 10 shows additional representative scanning electron micrographs of dry TP cross-sections (C=collagen; H=heart; K=kidney; L=liver; M=muscle; O=ovary; U=uterus; scale bar is 100 μm).

TP Structural Characteristics

Each tissue paper is defined by its own unique microstructure, similar to the distinct nature of native tissue and organs. As can be seen below, microstructures vary from being relatively flat with limited porosity (muscle and skin), to being highly porous and rough (Kidney and Uterus). Using the inherent autofluorescence of collagen, confocal fluorescence microscopy was utilized to map the topography and collagen distribution in each tissue paper (bottom), which illustrates diverse structures and shows that TP composition is dominated by collagen and not the PLGA binder.

Figure 2:
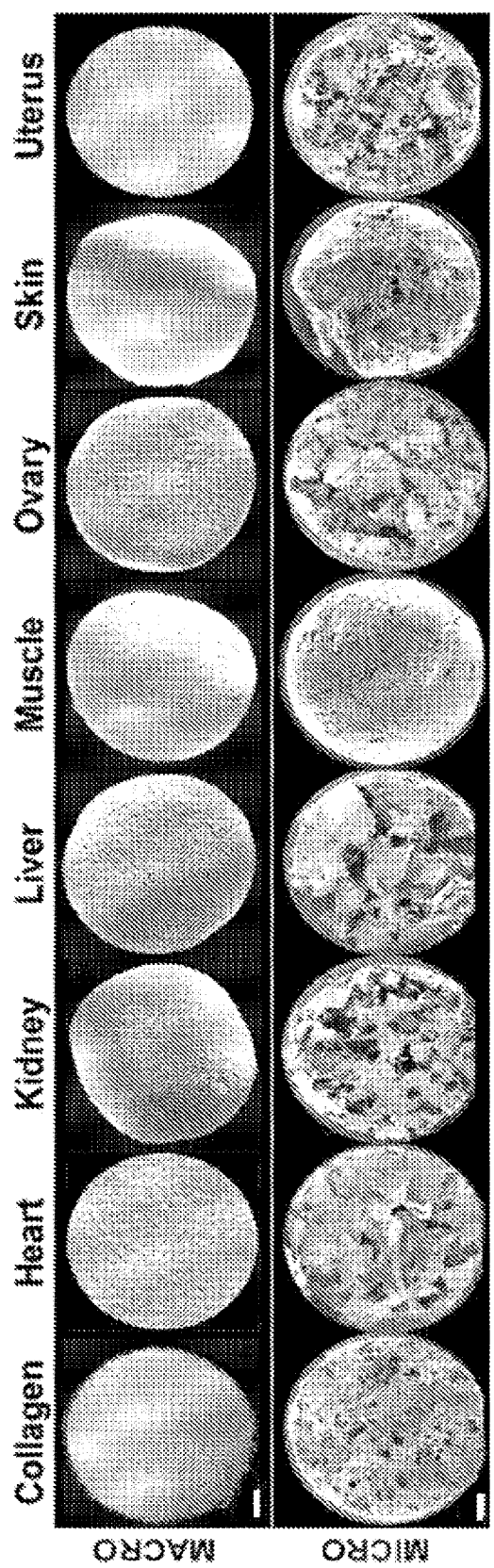
FIG. 2 includes images of the various TPs. The top row shows 7 cm diameter TPs, each made from 0.33 g of powdered dECM (scale is 1 cm). The middle row shows scanning electron micrographs (SEM) of the surfaces of 2 mm diameter punches obtained from the respective TPs in the top row (scale is 250 µm).
Figure 3:
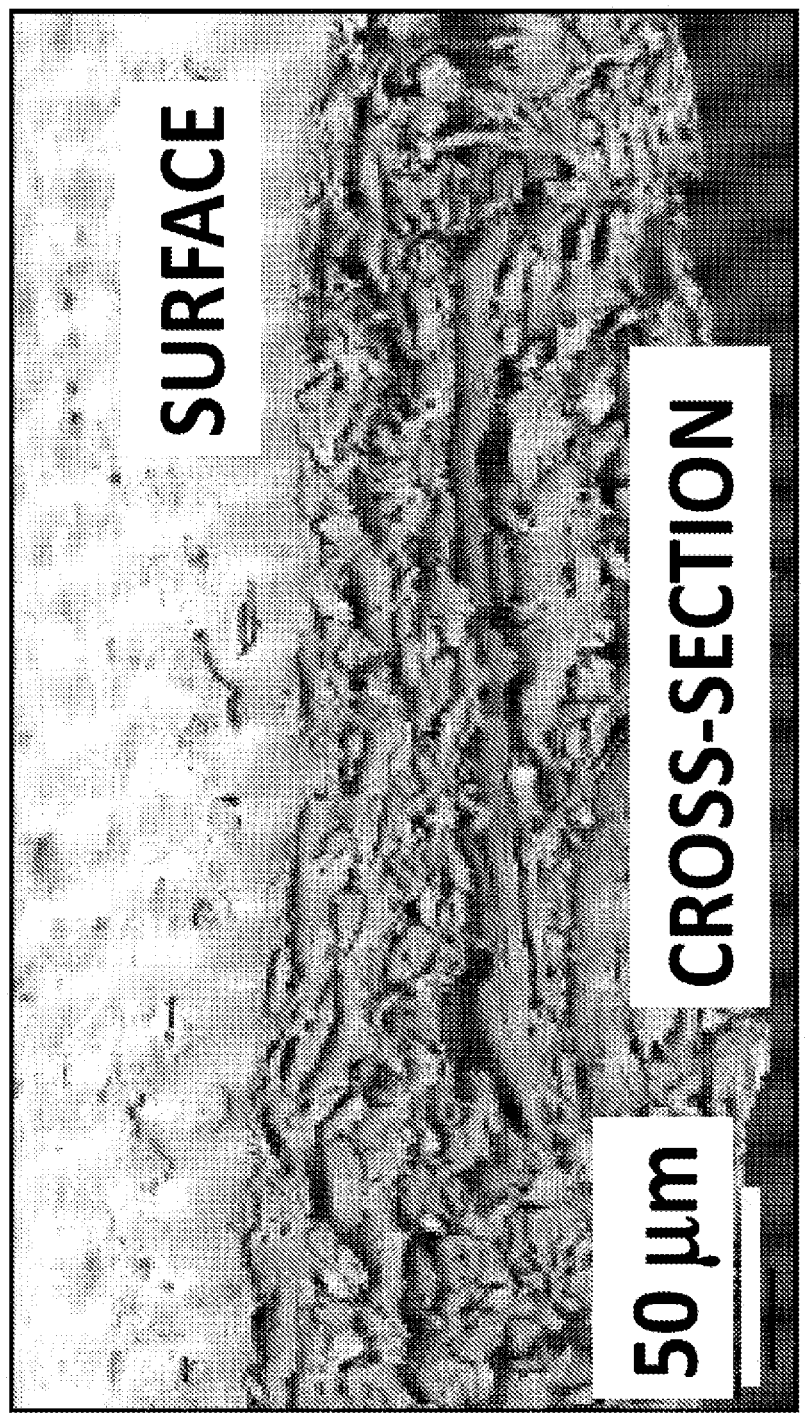
FIG. 3 shows a scanning electron micrograph (SEM) of muscle TP cross-section. Like natural muscle, muscle TP exhibits a layered structure. The surface of the muscle TP is labeled at the top of the image; the scale is 50 µm.

FIG. 2 includes images of the various TPs. The top row shows 7 cm diameter TPs, each made from 0.33 g of powdered dECM (scale is 1 cm). The middle row shows scanning electron micrographs of the surfaces of 2 mm diameter punches obtained from the respective TPs in the top row (scale is 250 μm). The bottom row, which is not shown, included topographical collagen maps of a representative region from each TP obtained via confocal microscopy using the native autofluorescence of collagen.

FIG. 3 shows a scanning electron micrograph (SEM) of muscle TP cross-section. Like natural muscle, muscle TP exhibits a layered structure. The surface of the muscle TP is labeled at the top of the image; the scale is 50 μm.

TP Mechanical, Handling and Physical Properties

Despite being comprised of majority ECM powder (65-70 vol. %), the resulting tissue papers remain mechanically robust in both dry and hydrated conditions. Like standard office paper, sheets of tissue paper can be crumpled and crumpled, cut, and folded. These characteristics, in addition to being able to be sutured to soft tissues, are highly advantageous for surgical implementation. Like structure, however, each tissue paper has unique mechanical properties that reflect to some degree the mechanical properties and function of the native tissue/organ from which they are derived (i.e., Muscle is mechanically strong, ovary is weaker).

Figure 4:
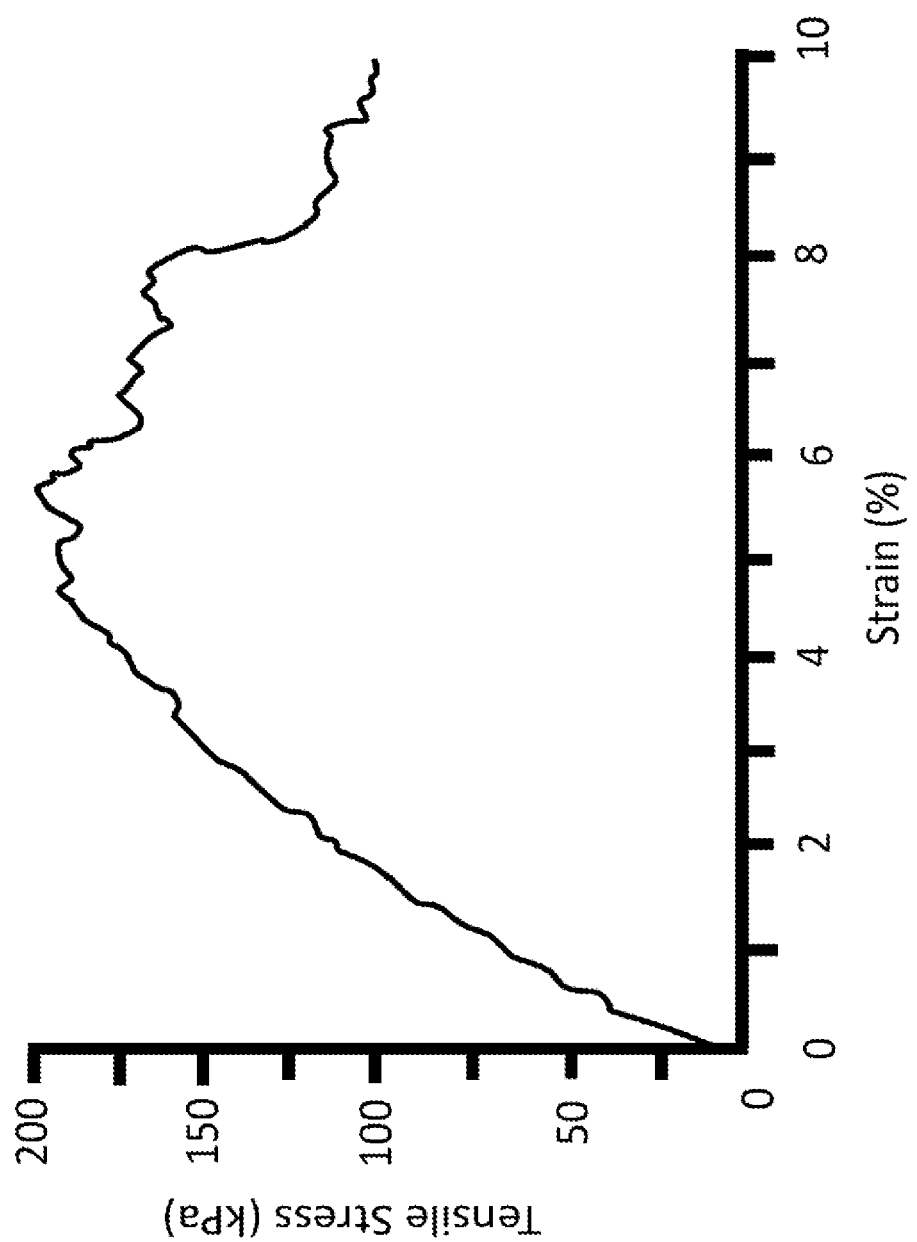
FIG. 4 shows a representative tensile mechanical loading curve for dry muscle tissue paper (E=5.5 MPa).

By way of illustration, photographs of dry muscle TP (from about 1 g of decelled tissue; TP is about 175 μm thick) were taken (not shown), showing the TP being crumpled and crushed by hand followed by unfolding without tearing or breaking. FIG. 4 shows a representative tensile mechanical loading curve for dry muscle tissue paper (E=5.5 MPa). Other photographs were taken (not shown), showing an ovary TP being cut with scissors, folded into an origami crane, and sutured to a fresh bovine ovary.

Figure 5A:
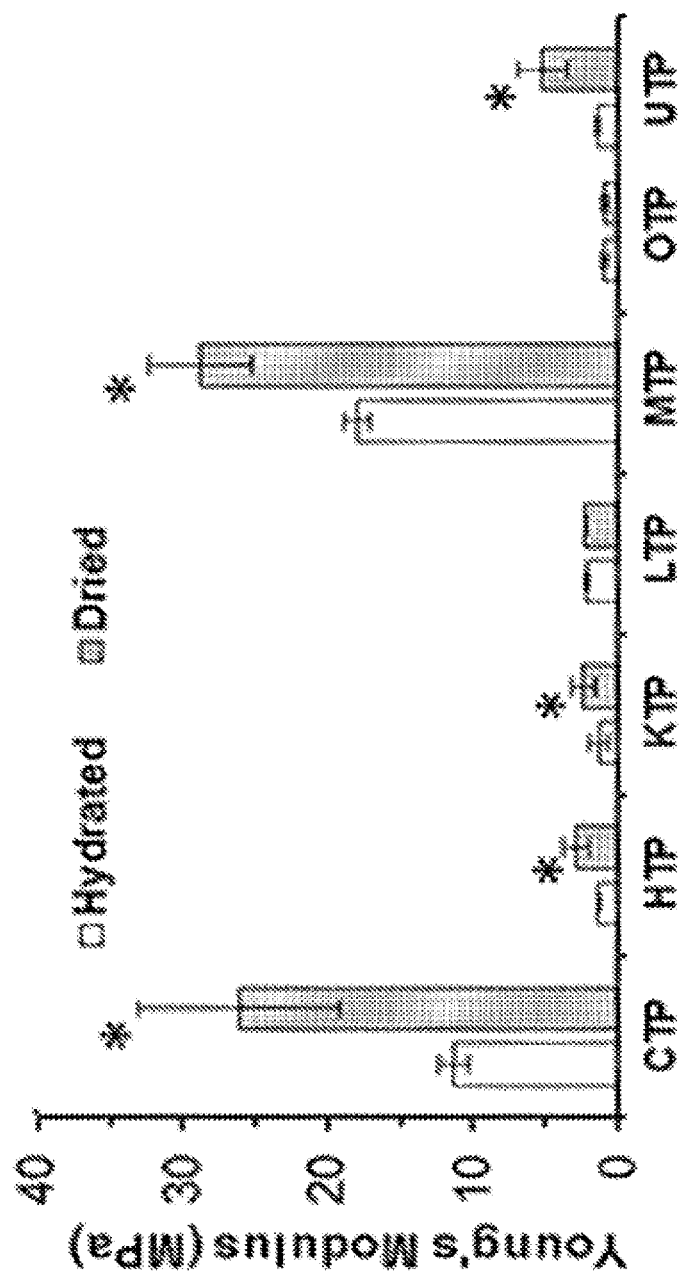
FIG. 5A shows elastic moduli for dry and hydrated tissue papers.
Figure 5B:
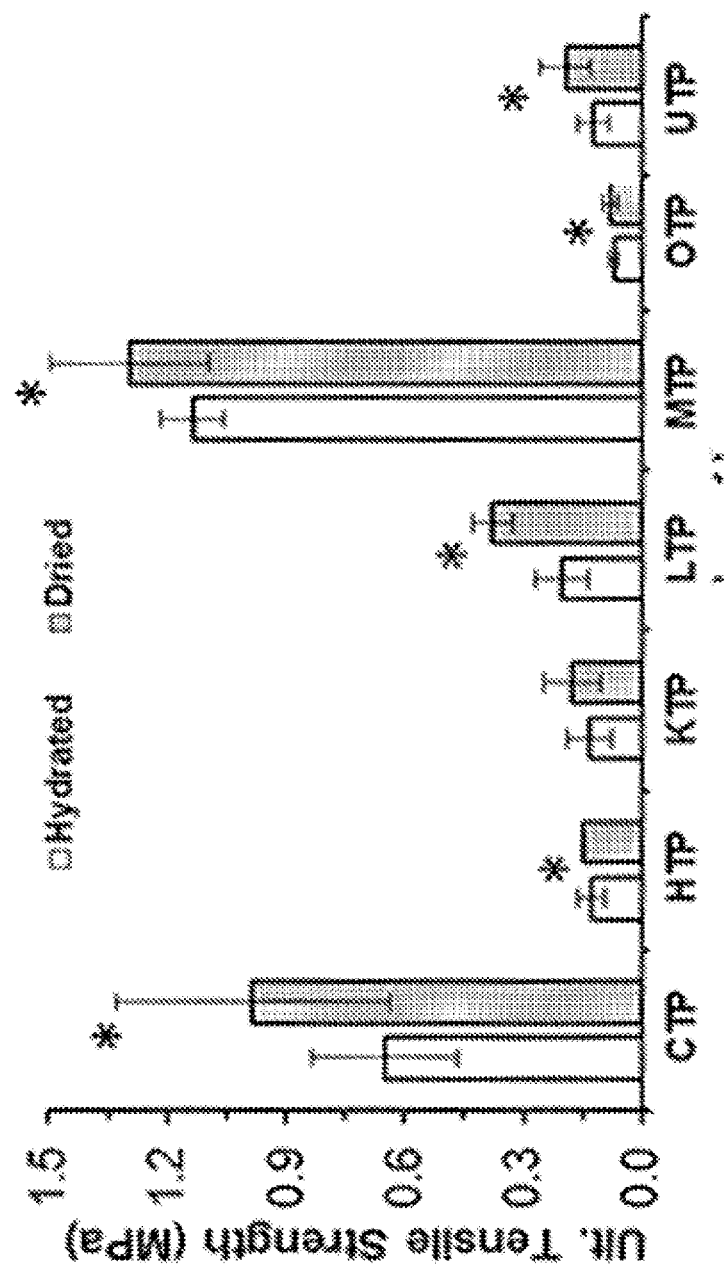
FIG. 5B shows ultimate tensile strengths of the dry and hydrated tissue papers of FIG. 5A.
Figure 5C:
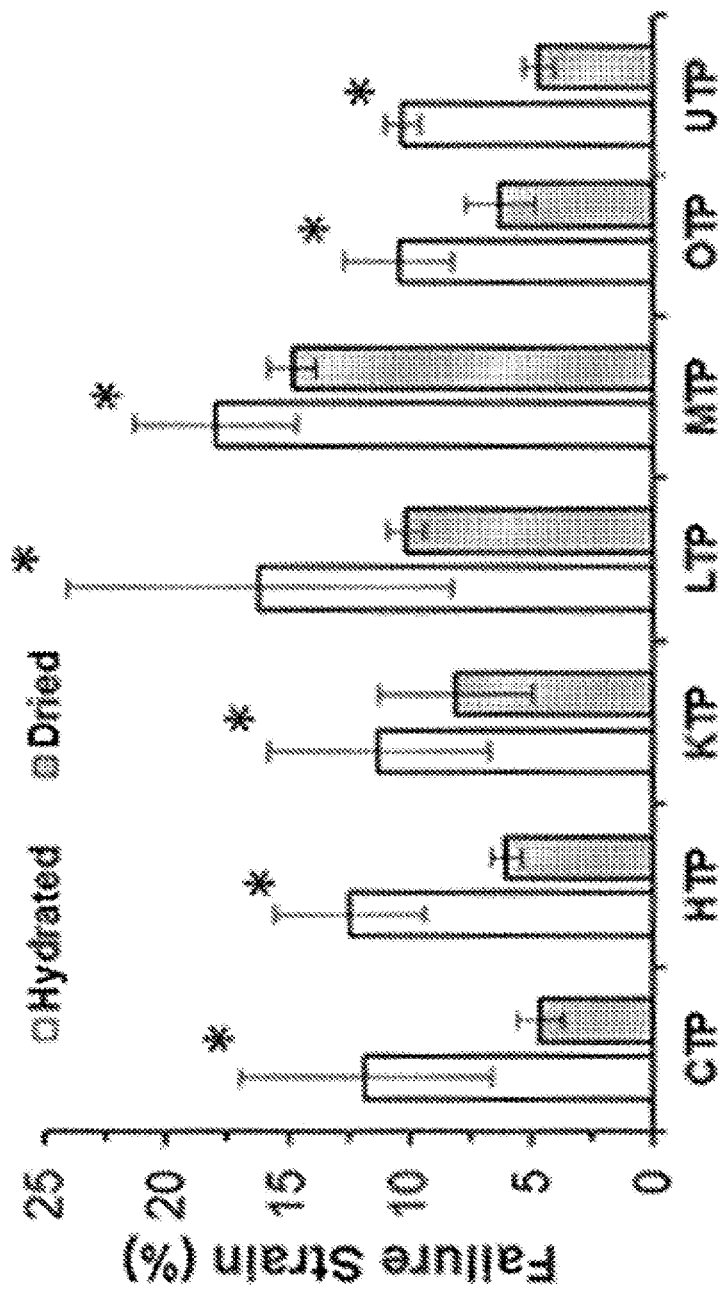
FIG. 5C shows the percent tensile strain to failure of the dry and hydrated tissue papers of FIG. 5A. * The symbol (*) denotes statistically significant differences between groups. (C=collagen; H=heart; K=kidney; L=liver; M=muscle; O=ovary; U=uterus).

As shown in FIGS. 5A-5C, mechanical properties are dependent upon tissue type as well as dry or hydrated condition. As shown in FIG. 5A, elastic moduli for non-structural tissues such as ovary, kidney, liver, heart and uterus range from 1-3 MPa while elastic moduli structural tissues such as muscle (as well as the collagen control) range as high as 20-30 MPa. This trend is also reflected in FIG. 5B showing ultimate tensile strengths of the TPs of FIG. 5A. Representative tensile curves of dry and hydrated tissue papers were obtained (data not shown). The average mechanical characteristics from these curves are plotted in FIG. 5A (modulus) and FIG. 5B (ultimate tensile strength).

Figure 6:
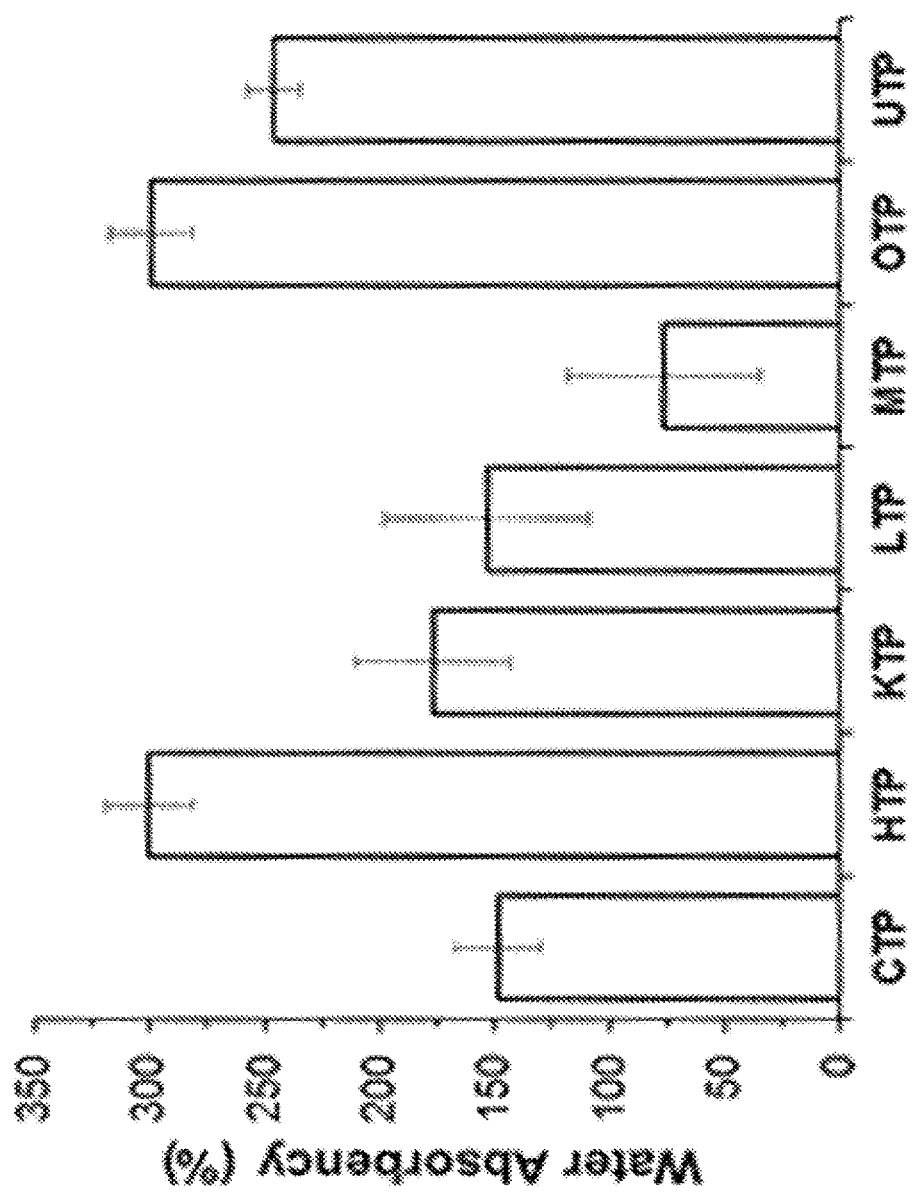
FIG. 6 shows the water absorbency of the TPs.

As shown in FIG. 6, the TPs are highly absorbent. TPs are capable of absorbing 175-400% their original dry weight in aqueous fluid. This is an ideal characteristic for biological use where the ability to soak up and retain surrounding fluids, including blood and plasma, is vital for tissue repair and regeneration.

In Vitro: Human Mesenchymal Stem Cells on TP

To determine if the individual tissue papers support cell attachment, growth and proliferation, and to elucidate the potential for tissue paper, specific cellular differentiation, adult human bone marrow mesenchymal stem cells were statically seeded (12 k/4 mm) onto TPs and cultured in standard DMEM with 10% FBS for up to 28 days. Live/dead scanning fluorescence confocal microscopy indicates that hMSCs adhere and proliferate on all TPs, except skin, to coat both sides of the samples by day 28. We later determined that skin had not been fully decelled prior to use. Additionally, by day 14, distinct cell morphologies were apparent on multiple TP types, indicating TP specific bioactivity.

Figure 7:
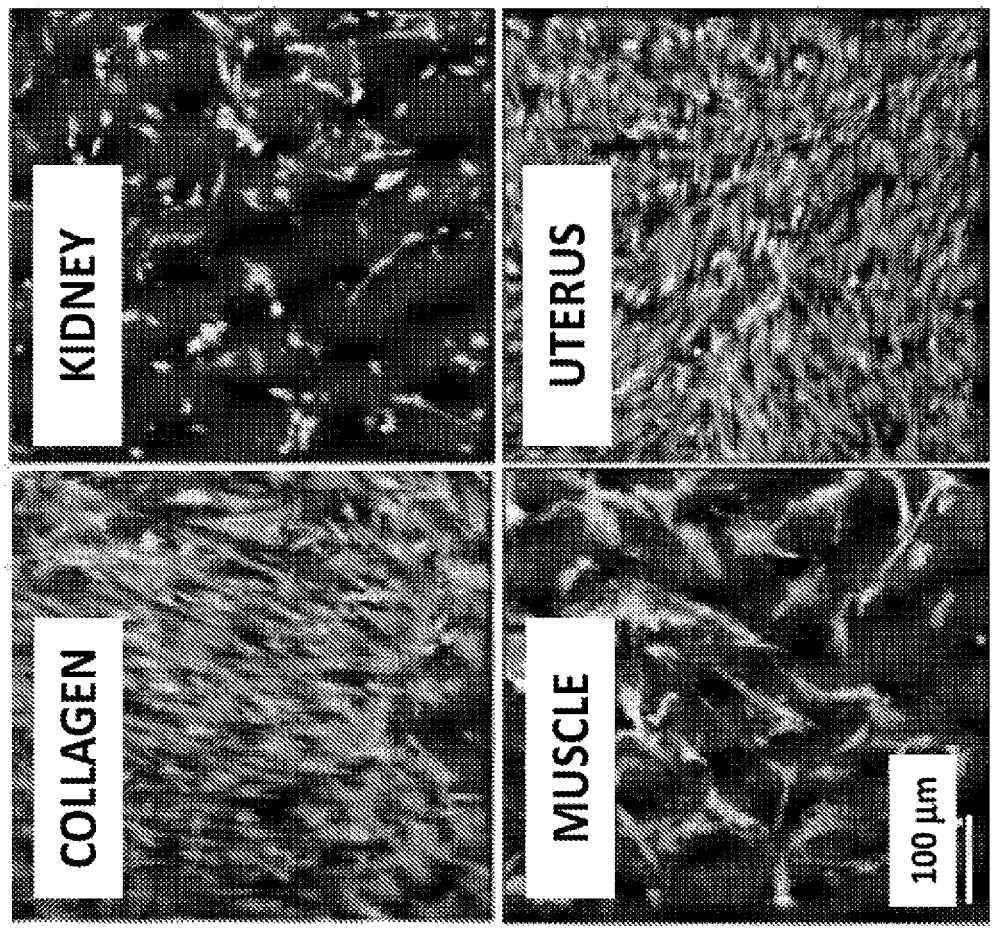
FIG. 7 shows images obtained via collagen autofluorescence. The images are zoomed in views of day 14 samples of four TPs, illustrating that TPs support human stem cell viability, proliferation, and highlighting the different hMSC (human mesenchymal stem cell) morphologies on different TPs (scale is 100 mm).

Top-down-views of 3D-reconstruction of confocal stacks illustrating hMSCs on TPs at day 1, day 14 and day 28 were obtained (data not shown). Green (light shading in the black and white images) indicated live cells; red indicated dead cells (the images show substantially no red); and blue indicates the tissue paper substrate (from collagen autofluorescence). FIG. 7 shows a zoomed in view of day 14 samples of four TPs, illustrating the different hMSC morphologies (scale is 100 μm). High-magnification, scanning electron micrographs of hMSCs on tissue papers 14 and 28 days after initial seeding were obtained (data not shown).

In Vitro: Hepatocytes and Ovarian Follicles

To investigate cell/tissue specific interactions with relevant cell types, initial in vitro experiments were performed using HUH7 (hepatocytes) on 12 mm punches of liver tissue paper, and freshly isolated mouse ovarian follicles on ovary TP. HUH7 adhered and proliferated to coat both sides of the liver TP by day 7 and maintained viable at least up until day 58. Mouse follicles on ovarian TP also adhered, remained viable, and matured over the course of 8 weeks. The health of ovarian follicles on cast PLGA sheets rapidly deteriorated. These results indicate that TPs may be used as tissue/organ specific materials in vitro and in vivo.

Collagen autofluorescence images were obtained showing the results with HUH7 on liver TP at day 7 and day 58 (data not shown). Live-dead confocal reconstructions of ovarian follicles on PLGA substrate and ovary TP substrate four days after seeding were also obtained (data not shown). The image of the ovary TP substrate showed a healthy ovarian follicle. An SEM image of the ovarian follicle was also obtained (data not shown).

Additional TP Manipulation and Integration with 3D-Printed Biomaterial Systems

Figure 8:
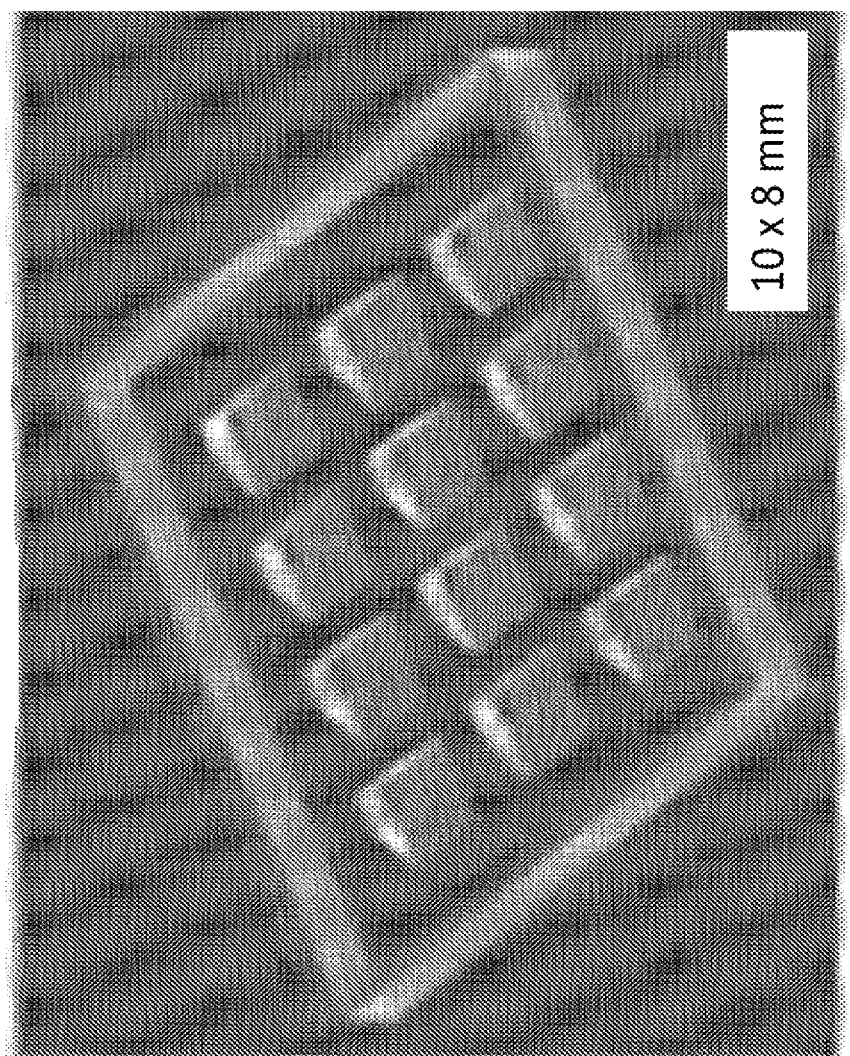
FIG. 8 is a digital image for forming a mold using additive manufacturing, e.g., 3D-printing, the mold to be used as a substrate for forming a scaffold.

Beyond simple, planar sheets, the dECM inks can be utilized in a number of ways. This includes being cast into 3D-printed molds to add texture and additional features. FIG. 8 shows a digital image of a mold used to form a 3D printed silicone mold. The mold was used as a substrate to cast an ovary dECM ink as described above. The ovary TP now includes larger depressions due to the projections in the silicone mold. A collagen depth map was obtained to demonstrate the shape of one of the "wells" of the ovary TP (data not shown). Another use involves modifying the dECM ink with other particles, such as calcium phosphates or conductive graphene prior to being cast into a tissue paper (images of graphene additive with cardiac dECM and calcium phosphate additive with muscle dECM not shown). In addition, individual sheets of TP (e.g., 200 μm thick each) can be laminated together (e.g., 6 sheets, 15 sheets, etc.) to create thicker and/or multi-tissue constructs (images not shown). Tissue papers can also be used as a 3D-printing substrate for the other 3D-printable inks described above, e.g., hyperelastic bone may be 3D printed onto skin TP and graphene may be 3D printed onto muscle TP (images not shown). Finally, TPs can even be grafted onto 3D-printed objects produced from the 3D-printable inks described above to form composite structures. In this manner, complex, multi-tissue composites, such as those comprised of muscle dECM TP, hyperelastic bone (3D-printed to form a skull), and graphene (3D-printed to form a wire) can be produced with ease (images not shown).

Supplementary Materials and Methods

Histology of Decellularized Tissue Pieces

Decellularized and lyophilized tissue pieces were sampled from each of the six tissues/organs (heart, kidney, liver, muscle, ovary, uterus) and transferred to 10% formalin for 1-2 weeks. Embedding, sectioning, and hematoxylin and eosin staining was performed by Northwestern University's Mouse Histology and Phenotyping Laboratory using established standard histological protocols. All histology slides were imaged using an upright optical microscope (Leica).

Absorbency 6 mm diameter disks of each tissue paper (n=5) were produced from larger 7 cm diameter sheets using biopsy punches. Individual disks were massed in their dry state using a high precision balance (dry weight). The disks were individually submerged in water for up to 5 minutes, removed, and shaken dry prior to massing again (wet weight). These values were used to determine absorbency ([wet weight−dry weight]/[dry weight]*100). The average absorbency and standard deviation was obtained from the five samples for each tissue paper type.

Mechanical Testing and Analyses

A 20 mm gauge-length tensile specimen, stainless steel stamp was used to cut tensile specimens out of the 7 cm diameter circles. TPs were mechanically tested under tensile conditions in both dry and hydrated (soaked in water for 5 minutes, excess water shaken off prior to testing) form (n=4 for both dry and hydrated for each tissue paper) using a LF Plus Mechanical Tester (Lloyed Instruments LLC), at a displacement rate of 2 mm/min until fracture. Elastic moduli were determined using the standard 0.2% offset approach. Ultimate tensile strength was determined as the highest stress value achieved for each samples. Failure strain was determined as the strain at which the sample fractured. All results were averaged and two-tailed, equal variance t-tests were used to determine significance between hydrated and dry mechanical properties for a given TP type.

Mechanical Manipulation

A roughly 10×0 cm sheet of uterine paper was cut using a standard scissors, and folded, following origami methods to make a crane. A small piece of OTP was soaked in dilute alamar blue prior to suturing to the surface of a fresh bovine ovary.

Mouse Follicle Isolation and Culture

CD1 mice (Harlan) were treated in accordance with Northwestern University's Animal Care and Use Committee policies. Small secondary follicles were mechanically isolated from day 12-15 mice as described previously (M. M. Laronda, A. E. Jakus. K. A. Whelan, J. A. Wertheim, R. N. Shah, T. K. Woodruff, Biomaterials 2015, 50, 20). Briefly, follicles were micro-dissected using insulin needles in dissection medium consisting of L15 (Gibco, 11415-064) supplemented with 0.5% penicillin, streptomycin (Corning 30-002-C) 1% fetal bovine serum (FBS, Gibco 10082-147) onto a 6 mm biopsy punch of OTP in 12 mm transwells (Millipore, PICM01250) in the wells (Corning, 353047) with media and cultured for 4 days with ½ of spent media replaced every other day. Ovary culture media consisted of alpha-MEM (Gibco, 32561) supplemented with 3 mg/ml bovine serum albumin (BSA, MP Biomedicals 103700), 0.5 mg/ml bovine fetuin (Sigma-Aldrich, F3385), 5 μg/ml insulin, 5 μg/ml transferrin, 5 ng/ml selenium (ITS, Sigma, 11884-1v1), and 10 mIU/ml follicle stimulating hormone (FSH, Abcam, ab51888).

Immunofluorescence Analysis of OTP and Primate and Human Cortical Strip Cultures Slides for immunofluorescence were prepared as described previously (A. E. Jakus, E. B. Secor, A. L. Rutz, S. W. Jordan, M. C. Hersam, R. N. Shah, Acs Nano 2015, 9, 4636). Briefly, they were blocked and permeabilized with 2% donkey serum, 1% BSA, 0.1% cold fish skin gelatin, 0.1% Triton, 0.05% Tween-20, 0.05% sodium azide in PBS for 1 hour and incubated in primary anti-vasa (1:50 diluted in 10% block solution, DDX4/MVH, Abcam, ab13840) at 4° C. overnight. Negative controls without primary antibodies were also analyzed to determine level of fluorescent background from the procedure. Both groups were incubated with an anti-rabbit AlexaFluor secondary 488 conjugate (1:500; Life Technologies. A2120). Sections were imaged on a Nikon E600 Fluorescent microscope (Nikon Instruments) with a Retiga Exi Fast 1394 camera (QImaging). Mounting medium with DAPI counterstain (Vector Laboratories, H-1200) was used to visualize nuclear material. This experiment was performed 2 times with one slide per time point (week 0, 1, 2, 8), each slide having four sections.

Immunofluorescence analysis of primate ovarian cortical strip tissue cultured on ovarian tissue paper was conducted (data not shown). Ovarian cortical tissue from one human participant and 1 rhesus macaque participant revealed multiple vasa-positive oocytes within fresh tissue pieces and pieces cultured for 1, 2 and 8 weeks.

In the primate ovarian cortex culture, ovarian cortical pieces were sliced into 0.5 mm thick slices and cut into 4×4 mm pieces. These were cultured on top of ovarian tissue paper that was cut to 6 mm diameter circles. These were both placed on a transwell and cultured for up to 8 weeks. Ovarian cortical tissue pieces from each of the two human and two rhesus macaque participants were sectioned after fresh isolation, or cultured for 1, 2 or 8 weeks. H & E sections from this tissue was examined as described previously (M. M. Laronda, F. E. Duncan, J. E. Hornick, M. Xu, J. E. Pahnke, K. A. Whelan, L. D. Shea, T. K. Woodruff, Journal of Assisted Reproduction and Genetics 2014, 31, 1013) in order to determine if the tissue was healthy or comprised of mostly dead cells. 100% of all the tissue for all of the groups examined (humans A, B and rhesus A,B) were considered healthy (data not shown).

Table 1, below, provides the ovarian tissue participant information.

TABLE 1

Ovarian tissue participant information.

| Participant | Age at death (years) | Diagnosis | Prior treatment |
| --- | --- | --- | --- |
| Human A | 30-40 | COD: stroke | No cancer history |
| Human B | 40-45 | Motor vehicle accident | No cancer history |
| Rhesus A | 2.44 | n/a | Used in a low pathogenic shigella study |
| Rhesus B | 3.25 | n/a | Used in a low pathogenic shigella study |

Silicone Mold Design, 3D-Printing, and Tissue Paper Casting

The silicone mold was digitally designed using proprietary software provided by Envisiontec GmbH and associated directly with 3D-BioPotter. White silicone caulk (ACE Hardware), was loaded into the extrusion cartridge and 3D-printed under ambient conditions using a 200 µm nozzle into the pre-defined shape. The mold was permitted to dry overnight prior to being used for casting. Ovary dECM ink was prepared as previously described and cast into the silicone mold. Excess material was used to ensure volumetric filling of the mold. Excess, dried material around the edges was trimmed using a scalpel and discarded.

Hybrid Hydroxyapatite and Graphene Tissue Paper Fabrication

Tissue papers containing hydroxyapatite or graphene, along with muscle TP (MTP), were prepared in a similar fashion to the standard tissue papers. The MTP+HA tissue paper was prepared by replacing half the volume of the usual MTP powder with an equivalent volume of HA. MTP+graphene was prepared in the same manner, replacing half of the usual volume of MTP powder with equivalent volume of graphene. The resulting inks were vortexed for approximately one minute prior to casting to ensure homogeneity of the dECM and HA or graphene particles.

3D-Printing onto Tissue Papers

All 3D-printing was performed using a 3D-BioPlotter (Envisiontec GmbH). Hyperelastic Bone and 3D-Graphene inks were prepared and 3D-printed as previously described previously onto the surfaces of 2×2 cm squares of MTP (A. E. Jakus, E. B. Secor, A. L. Rutz, S. W. Jordan, M. C. Hersam, R. N. Shah, Acs Nano 2015, 9, 4636).

Grafting Tissue Paper onto 3D-Printed Objects

Muscle tissue paper (MTP) was grafted onto previously 3D-printed hyperelastic bone (see A. E. Jakus, A. L. Rutz, S. W. Jordan, A. Kannan, S. Mitchell, C. Yun, K. D. Koube, S. C. Yoo, H. E. Whiteley, C. P. Richter, R. D. Galiano, W. K. Hsu, S. R. Stock, E. L. Hsu, R. N. Shah. Science Translational Medicine 2016, in press) in the form of a human skull (design from open source CAD model of human CT scan) by applying several microliters of DCM to the surface of the skull and physically placing the MTP onto the site. Within a few seconds, the MTP had fully fused to the skull. The 3D-graphene ink wire (A. E. Jakus, E. B. Secor, A. L. Rutz, S. W. Jordan, M. C. Hersam, R. N. Shah, Acs Nano 2015, 9, 4636) was extruded by hand from a 5 mL syringe, connecting the two pieces of previously grafted MTP.

Example 2

Figure 11:
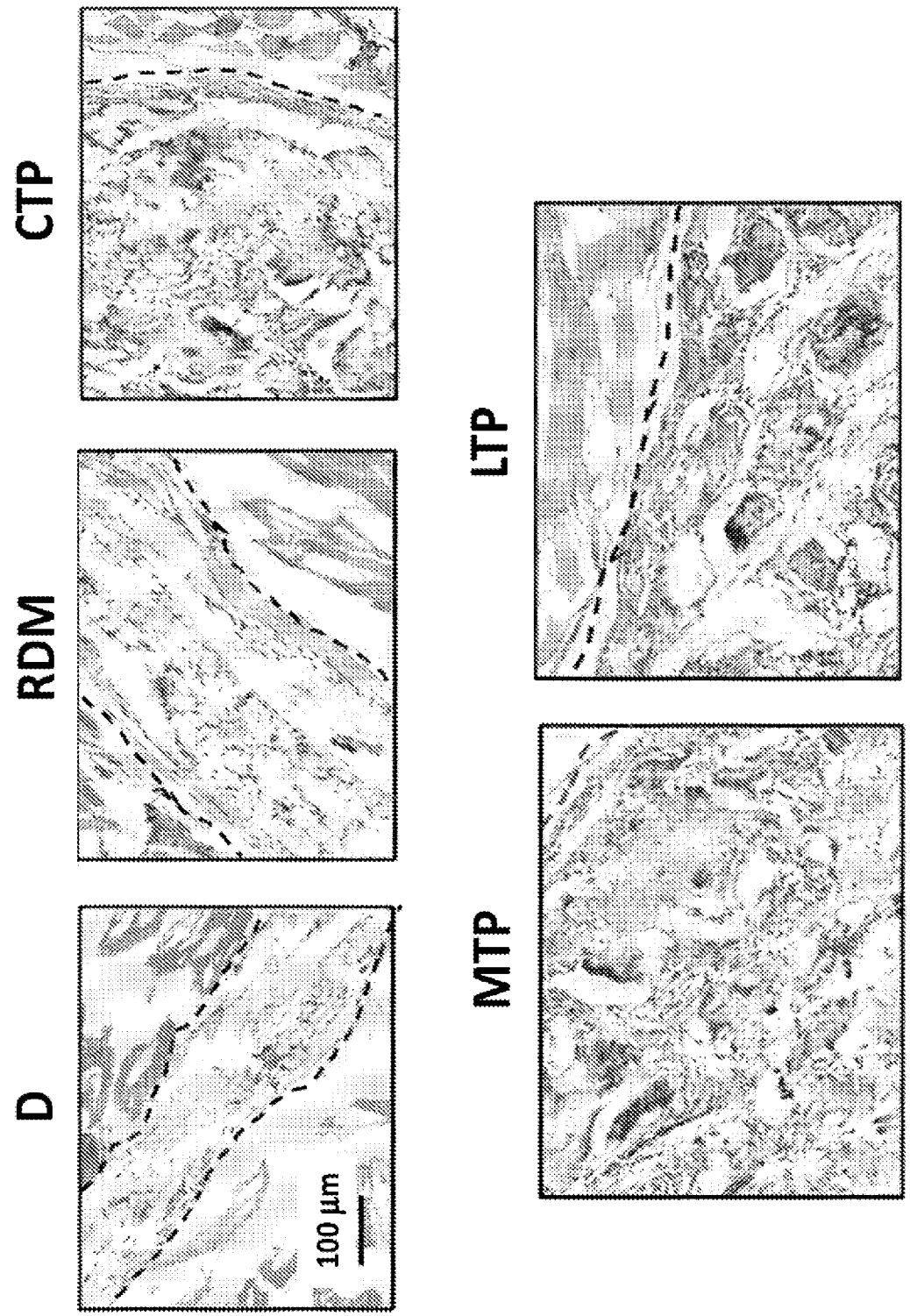
FIG. 11 shows Hematoxilin and Eosin (H&E) staining of explanted tissue papers and surrounding rat muscle tissues 6 weeks after implantation. Black dashed line denotes boundaries between native tissue and TP implant/defect. D corresponds to negative control, or the defect. RDM corresponds to the positive control, rat decellularized muscle matrix. Otherwise, C=collagen; M=muscle; L=liver.

This Example describes the results on a rat in vivo study. Eight-centimeter diameter liver, muscle, collagen tissue papers (LTP, MTP, CTP) were made. The LTP and MTP were derived from porcine liver and muscle tissues, respectively. The CTP was derived from bovine collagen tissue. In each case, the TPs were prepared as described in Example 1. Eight mm diameter punches from each TP (the critical size of the muscle defect) were placed randomly into previously made muscle defects in each rat (8 mm diameter muscle piece removed). Each rat (Sprague Dawley; n=4) contained five sample groups (LTP, MTP, CTP, rat decellularized muscle (RDM), and open defect (D)). TPs were secured in the muscle defect sites via 4 individual 7-0 sutures to surrounding native muscle tissue. The backs of the rats were closed via suturing and stapling. After 6 weeks, the rats were sacrificed and implants removed for histological analyses. Histology indicates that the TPs integrated well with surrounding muscle tissue and did not illicit an acute immune response, despite being fabricated from decellularized porcine or bovine (collagen) tissues. The histology results are shown in FIG. 11.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more".

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A method of forming a porous scaffold, the method comprising:
   depositing an ink onto the surface of a substrate by pouring or flowing the ink while applying no force to the ink other than gravity, the ink comprising an elastomer; an organic solvent system comprising an evaporant, a surfactant, and a plasticizer; and decellularized extracellular matrix (dECM) particles; and
   removing the organic solvent system from the ink to form a scaffold free of crosslinking between molecular components and that is not a gel,
   wherein the ink is a non-aqueous ink, and
   wherein the porous scaffold is sized and configured to be grafted.

2. The method of claim 1, wherein the deposition step is carried out at room temperature and atmospheric pressure.

3. The method of claim 1, wherein the deposition step provides a layer of deposited ink having a thickness of about 100 µm or greater.

4. A method of using the scaffold of claim 1, the method comprising implanting the scaffold in vivo into a patient or grafting the scaffold in vivo onto a tissue or an organ of the patient.

5. The method of claim 1, further comprising the step of cutting or folding the scaffold in a surgical application, wherein the scaffold is mechanically robust enough to maintain its structural integrity while undergoing the cutting or folding in the surgical applications, wherein retaining its structural integrity comprises not breaking, crumbling, flaking, or tearing.

6. The method of claim 1, further comprising the step of suturing the scaffold to biological tissue, wherein the scaffold is mechanically robust enough to retain its structural integrity while being sutured to the biological tissue, wherein retaining its structural integrity comprises not breaking, crumbling, flaking, or tearing.

7. The method of claim 1, further comprising the step of applying mechanical stress to the scaffold wherein the scaffold does not undergo a solid to liquid transition upon application of the mechanical stresses.

8. The method of claim 1, further comprising a step of deriving the dECM particles from an ovary, muscle, liver, heart, kidney, uterus, skin, or collagen.

9. The method of claim 1, further comprising a step of forming an external topography that is complementary to a pattern mold.

10. The method of claim 1, further comprising a step of laminating a plurality of scaffolds, wherein each one of the plurality of scaffolds are derived from the same or from a different type of dECM particles than any other one of the plurality of scaffolds.

11. The method of claim 1, further comprising a step of fusing the scaffold and another object containing a similar elastomer as the elastomer of the scaffold.

12. The method of claim 1, wherein the scaffold is substantially free of liquid.

13. The method of claim 1, wherein the scaffold comprises irregularly shaped pores having a random orientation and distribution throughout the scaffold.

14. The method of claim 1, wherein the scaffold, in a dry state, exhibits a Young's modulus in the range of from about 1 MPa to about 30 MPa.

15. The method of claim 1, wherein the scaffold, in a dry state, exhibits an ultimate tensile strength of from about 0.1 MPa to about 1.5 MPa.

16. The method of claim 1, wherein the scaffold exhibits an absorbency in the range of from about 100% to about 500%.

17. The method of claim 1, wherein the scaffold comprises from about 30% to about 80% by weight dECM particles, based on the total solids content of the scaffold, and from about 20% to about 70% by weight elastomer, based on the total solids content of the scaffold.

18. The method of claim 1, wherein the scaffold comprises a synthetic powder.

19. A method of using the scaffold of claim 1, the method comprising use with cells, a tissue, or an organ.

20. The method of using the scaffold of claim 19, the method comprising supporting a population of human mesenchymal stem cells, hepatocytes or ovarian follicles at the scaffold, wherein the population retains its viability over a period of at least 28 days when the scaffold is cultured in vitro.

21. The method of using the scaffold of claim 19, the method comprising supporting ovarian tissue at the scaffold, wherein the ovarian tissue retains its viability over a time period of at least 8 weeks and supports development of one or more vasa-positive oocytes from the ovarian tissue when the scaffold is cultured in vitro.

22. The method of using the scaffold of claim 19, the method comprising supporting muscle tissue at the scaffold, wherein the muscle tissue retains its viability by integrating with the scaffold.

* * * * *

UNITED STATES PATENT AND TRADEMARK OFFICE
CERTIFICATE OF CORRECTION

PATENT NO. : 11,904,071 B2
APPLICATION NO. : 17/330762
DATED : February 20, 2024
INVENTOR(S) : Adam E. Jakus and Ramille N. Shah It is certified that error appears in the above-identified patent and that said Letters Patent is hereby corrected as shown below:

In the Specification

Column 3, Line 25, where the phrase "from IS vol %" should be replaced with "from 15 vol %".

Column 4, Line 51, where the phrase "1 pin or less" should be replaced with "1 µm or less".

Column 5, Line 66, where the phrase "about 200 m" should be replaced with "200 µm".

Column 6, Line 1, where the phrase "about 100 sim" should be replaced with "about 1 µm".

Column 7, Line 8, where the phrase "This is b) contrast" should be replaced with "This is by contrast".

Column 11, Line 66, where the phrase "roughly 10×0 cm sheet" should be replaced with "roughly 10×10 sheet".

Column 12, Line 8, where the phrase "from day 12-15 mice" should be replaced with "from day 12 — 15 mice".

Signed and Sealed this
Second Day of April, 2024

Katherine Kelly Vidal
*Director of the United States Patent and Trademark Office*